US011175292B2

(12) United States Patent
Yasui et al.

(10) Patent No.: US 11,175,292 B2
(45) Date of Patent: Nov. 16, 2021

(54) ANTI-HUMAN HEMOGLOBIN MONOCLONAL ANTIBODY OR ANTIBODY KIT, INSOLUBLE CARRIER PARTICLE TO WHICH ANTI-HUMAN HEMOGLOBIN MONOCLONAL ANTIBODY IS IMMOBILIZED, AND MEASUREMENT REAGENT AND MEASUREMENT METHOD USING SAME

(71) Applicant: EIKEN KAGAKU KABUSHIKI KAISHA, Tokyo (JP)

(72) Inventors: Ryota Yasui, Tochigi (JP); Megumi Yui, Tochigi (JP); Mitsuru Makinodan, Tochigi (JP); Yasuhiro Seki, Tochigi (JP); Chisa Sakanishi, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 318 days.

(21) Appl. No.: 16/305,041

(22) PCT Filed: May 26, 2017

(86) PCT No.: PCT/JP2017/019736
§ 371 (c)(1),
(2) Date: Nov. 27, 2018

(87) PCT Pub. No.: WO2017/209001
PCT Pub. Date: Dec. 7, 2017

(65) Prior Publication Data
US 2020/0319183 A1    Oct. 8, 2020

(30) Foreign Application Priority Data

May 30, 2016 (JP) .............................. JP2016-107343

(51) Int. Cl.
*G01N 33/557* (2006.01)
*G01N 33/545* (2006.01)
*G01N 33/553* (2006.01)
*G01N 33/574* (2006.01)
*G01N 33/72* (2006.01)
*G01N 33/546* (2006.01)
*C07K 16/18* (2006.01)
*G01N 33/577* (2006.01)

(52) U.S. Cl.
CPC ......... *G01N 33/577* (2013.01); *G01N 33/545* (2013.01); *G01N 33/546* (2013.01); *G01N 33/553* (2013.01); *G01N 33/57419* (2013.01); *G01N 33/721* (2013.01); *C07K 16/18* (2013.01)

(58) Field of Classification Search
None
See application file for complete search history.

(56) References Cited

U.S. PATENT DOCUMENTS

| 6,524,583 | B1* | 2/2003 | Thorpe ................... A61P 31/18 424/145.1 |
| 2008/0227208 | A1* | 9/2008 | Yee ........................ G01N 33/72 436/66 |
| 2011/0129860 | A1* | 6/2011 | Karl ................. G01N 33/57419 435/7.92 |
| 2011/0136261 | A1 | 6/2011 | Fujita et al. |
| 2015/0219658 | A1 | 8/2015 | Scheefers et al. |

FOREIGN PATENT DOCUMENTS

| CN | 101236210 A | 8/2008 |
| JP | S61137064 A | 6/1986 |
| JP | H02193071 A | 7/1990 |
| JP | H5-322888 A | 12/1993 |
| JP | 2001-221800 A | 8/2001 |
| JP | 2010-014586 A | 1/2010 |
| JP | 2011-503593 A | 1/2011 |
| JP | 4926320 B2 | 5/2012 |
| KR | 20150036388 A | 4/2015 |
| TW | I235159 B | 7/2005 |
| WO | 2009/065551 A1 | 5/2009 |
| WO | 2010/013525 A1 | 2/2010 |

OTHER PUBLICATIONS

Patent Cooperation Treaty, English Translation of International Report on Patentability and Written Opinion for PCT/JP2017/019736, dated Dec. 13, 2018, pp. 1-6.

(Continued)

*Primary Examiner* — Ellen J Marcsisin
(74) *Attorney, Agent, or Firm* — Pillsbury Winthrop Shaw Pittman LLP (57) ABSTRACT

The present invention provides an anti-human hemoglobin monoclonal antibody or an antibody kit for specifically detecting and measuring a hemoglobin-haptoglobin complex in a sample with ease, and an insoluble carrier particle to which the monoclonal antibody is immobilized, and a measurement reagent and a measurement method for specifically detecting and measuring a hemoglobin-haptoglobin complex in a sample using the same. The anti-human hemoglobin monoclonal antibody of the present invention does not react to free hemoglobin or free haptoglobin which is not formed in a complex, but specifically reacts to a hemoglobin-haptoglobin complex when the antibody is immobilized to an insoluble carrier particle and used.

5 Claims, 1 Drawing Sheet

(56) References Cited

OTHER PUBLICATIONS

European Patent Office, Extended European Search Report for EP Application No. 17806556.1, dated Oct. 11, 2019, pp. 1-8.
Horn et al, "Generation of a haptoglobin-hemoglobin complex-specific Fab antibody blocking the binding of the complex to CD163", European Journal of Haematology, Oct. 1, 2003, pp. 289-293, vol. 71, No. 4.
Takashi Meguro, "Measurement of Fecal Hemoglobin-Haptoglobin Complex as a New Diagnostic Tool of Lower Gastrointestinal Tract Diseases", Hokkaido Journal of Medical Science, Jul. 1994, vol. 69, No. 4, pp. 995 to 1009, p. 1006, English Abstract.
Yasushi Hamaya, "Performance of hemoglobin-haptoglobin complex detection in feces for colorectal cancer screening", Journal of Gastroenterological Cancer Screening, 2012, vol. 50, No. 3, pp. 345 to 350, English Abstract.
Chalkias, Athanasios, Patients with colorectal cancer are characterized by increased concentration -of fecal hb-hp complex, myeloperoxidase, and secretory IgA, Am J Clin Oncol, Dec. 2011, vol. 34 No. 6, p. 561-566, Materials and Methods (Measurement of Fecal Hb-Hp Complex, MPO, and sigA).
International Search Report for PCT/JP2017/019736, dated Aug. 8, 2017, pp. 1-2, English Translation.
Korean Intellectual Property Office, Official Action issued in KR Patent Application No. 10-2018-7037157, dated Mar. 23, 2021, pp. 1-6.

\* cited by examiner

ANTI-HUMAN HEMOGLOBIN MONOCLONAL ANTIBODY OR ANTIBODY KIT, INSOLUBLE CARRIER PARTICLE TO WHICH ANTI-HUMAN HEMOGLOBIN MONOCLONAL ANTIBODY IS IMMOBILIZED, AND MEASUREMENT REAGENT AND MEASUREMENT METHOD USING SAME

RELATED APPLICATIONS

This patent application is a national stage entry of, and claims priority to International Patent Application No. PCT/JP2017/019736 filed May 26, 2017, and published as International Patent Publication WO/2017/209001 on Dec. 7, 2017, which claims priority to Japanese Patent Application No. JP 2016-107343 filed May 30, 2016. The entire content of the foregoing applications is incorporated herein by reference, including all text, tables and drawings.

TECHNICAL FIELD

The present invention relates to an anti-human hemoglobin monoclonal antibody or an antibody kit causing an agglutination reaction specifically with a hemoglobin-haptoglobin complex in a test specimen containing the hemoglobin-haptoglobin complex when the antibody or the kit is immobilized to an insoluble carrier particle, an anti-human hemoglobin monoclonal antibody-immobilized insoluble carrier particle, and a measurement reagent and a measurement method for specifically detecting and measuring a hemoglobin-haptoglobin complex in a test specimen using the same.

BACKGROUND ART

Inflammations, tumors, cancers, and the like are known as digestive organ diseases involving bleeding. Consequently, a fecal occult blood test investigating the presence of hemoglobin in a feces is carried out as a screening examination for these diseases. Further, this examination is carried out mainly by an immunoassay (Japanese Unexamined Patent Publication No. S61-137064).

However, hemoglobin contained in feces is decomposed by various factors beginning with bacteria contained in the feces, i.e., a test specimen, and also while travelling through the digestive tracts and becomes unable to be detected and measured. For this reason, the detection and the measurement of hemoglobin in feces are effective for examining bleeding in the descending colon and rectum, but it is difficult to examine bleeding in the upper digestive tracts.

Accordingly, a measurement of a hemoglobin-haptoglobin complex, which is not decomposed by various factors beginning with bacteria contained in feces, is proposed and carried out. However, the measurement principle thereof is a sandwich immunoassay wherein an antibody specifically binding to hemoglobin and an antibody specifically binding to haptoglobin are combined (Japanese Unexamined Patent Publication No. H2-193071).

Sandwich immunoassays represented by ELISA need an extended time for measurement because they include a washing step of removing protein components and the like other than components to be measured contained in a test specimen in the process of measurement. For this reason, these methods are not suitable for the detection and measurement wherein a large number of test specimens need to be subjected to the detection and measurement in a short time.

Additionally, the basic structures of hemoglobin and haptoglobin form tetramers, and thus when an antibody specifically binding to hemoglobin and an antibody specifically binding to haptoglobin obtained by a conventional method are applied in combination to an immunoassay by an agglutination method capable of subjecting a large number of test specimens to the detection and measurement in a short time, the agglutination reaction is caused with not only a hemoglobin-haptoglobin complex but also free hemoglobin and free haptoglobin which are not formed in a complex, thereby making an accurate measurement difficult.

Under the circumstances, it is desired to produce an antibody which is applicable to the immunoassay by an agglutination method and can detect and measure only a hemoglobin-haptoglobin complex without detecting and measuring free hemoglobin and free haptoglobin which are not formed in a complex, and to establish an immunoassay by an agglutination method using the antibody for specifically detecting and measuring a hemoglobin-haptoglobin complex.

SUMMARY OF INVENTION

Technical Problem

Performing a screening examination on digestive organ diseases involving bleeding has been an important issue to find at an early stage inflammations, tumors, cancers and the like which is becoming severe. Consequently, a reagent capable of detecting and measuring the hemoglobin-haptoglobin complex, which is not decomposed in the digestive tracts, in a large number of samples in a short time is in a demand.

Thus, the present invention has an object to provide an antibody which can specifically detect and measure a hemoglobin-haptoglobin complex in large number of samples in a short time without detecting and measuring free hemoglobin and free haptoglobin which are not formed in a complex, and which can be used for an immunoassay by an agglutination method.

Solution to Problem

The present inventors have conducted extensive studies to solve the above problem and found an antibody which does not react to free hemoglobin or free haptoglobin which is not formed in a complex but specifically reacts to a hemoglobin-haptoglobin complex when the antibody is bound to an insoluble carrier particle, whereby the present invention has been accomplished.

More specifically, the present invention comprises the following features.

(1) An anti-human hemoglobin monoclonal antibody, wherein a monoclonal antibody-immobilized insoluble carrier particle obtained by immobilizing the monoclonal antibody to an insoluble carrier particle causes an agglutination reaction with a hemoglobin-haptoglobin complex, but does not cause an agglutination reaction with hemoglobin.

(2) The anti-human hemoglobin monoclonal antibody according to (1), wherein the anti-human hemoglobin monoclonal antibody is 5C-2A (NPMD accession number NITE BP-02268) or 12-9G-C(NPMD accession number NITE BP-02269).

(3) An antibody kit comprising two or more anti-human hemoglobin monoclonal antibodies, wherein one or more monoclonal antibody-immobilized insoluble carrier particles, which are obtained by immobilizing the two or more anti-human hemoglobin monoclonal antibodies to one or more insoluble carrier particles, cause an agglutination reaction with a hemoglobin-haptoglobin complex, but do not cause an agglutination reaction with hemoglobin.

(4) The antibody kit according to (3), wherein the two or more anti-human hemoglobin monoclonal antibodies are two or more selected from the group consisting of 5C-2A (NPMD accession number NITE BP-02268), 7C-7B-8E (NPMD accession number NITE BP-02270), 1-5G-3C (NPMD accession number NITE BP-02271), 12-9G-C (NPMD accession number NITE BP-02269), 79-8G-3F (NPMD accession number NITE BP-02272), and SU112.

(5) The anti-human hemoglobin monoclonal antibody or the antibody kit according to any of (1) to (4), wherein the anti-human hemoglobin monoclonal antibody is derived from a mouse.

(6) A monoclonal antibody-immobilized insoluble carrier particle obtained by immobilizing one or more anti-human hemoglobin monoclonal antibodies to an insoluble carrier particle, wherein the monoclonal antibody-immobilized insoluble carrier particle causes an agglutination reaction with the hemoglobin-haptoglobin complex, but does not cause an agglutination reaction with hemoglobin.

(7) The monoclonal antibody-immobilized insoluble carrier particle according to (6), wherein the one or more anti-human hemoglobin monoclonal antibodies are one of 5C-2A (NPMD accession number NITE BP-02268) or 12-9G-C(NPMD accession number NITE BP-02269).

(8) The monoclonal antibody-immobilized insoluble carrier particle according to (6), wherein the one or more anti-human hemoglobin monoclonal antibodies are two or more selected from the group consisting of 5C-2A (NPMD accession number NITE BP-02268), 7C-7B-8E (NPMD accession number NITE BP-02270), 1-5G-3C (NPMD accession number NITE BP-02271), 12-9G-C(NPMD accession number NITE BP-02269), 79-8G-3F (NPMD accession number NITE BP-02272), and SU112.

(9) The monoclonal antibody-immobilized insoluble carrier particle according to any of (6) to (8), wherein the anti-human hemoglobin monoclonal antibody is derived from a mouse.

(10) The monoclonal antibody-immobilized insoluble carrier particle according to any of (6) to (9), wherein the insoluble carrier particle to which the monoclonal antibody is immobilized is a latex particle or a metal colloidal particle.

(11) An immunological measurement reagent for specifically detecting a hemoglobin-haptoglobin complex, comprising the monoclonal antibody-immobilized insoluble carrier particle according to any of (6) to (10).

(12) An anti-human hemoglobin monoclonal antibody, being 5C-2A (NPMD accession number NITE BP-02268), 7C-7B-8E (NPMD accession number NITE BP-02270), 1-5G-3C (NPMD accession number NITE BP-02271), 12-9G-C(NPMD accession number NITE BP-02269), or 79-8G-3F (NPMD accession number NITE BP-02272).

(13) An immunological measurement method for specifically detecting a hemoglobin-haptoglobin complex, comprising using the anti-human hemoglobin monoclonal antibody or the antibody kit according to any of (1) to (5), the monoclonal antibody-immobilized insoluble carrier particle according to any of (6) to (10), the immunological measurement reagent according to (11), or the anti-human hemoglobin monoclonal antibody according to (12).

(14) An immunological measurement method for specifically detecting a hemoglobin-haptoglobin complex, comprising using a monoclonal antibody-immobilized insoluble carrier particle obtained by immobilizing one or more anti-human hemoglobin monoclonal antibodies to an insoluble carrier particle, wherein the monoclonal antibody-immobilized insoluble carrier particle causes an agglutination reaction with the hemoglobin-haptoglobin complex, but does not cause an agglutination reaction with hemoglobin.

(15) The immunological measurement method according to (14), wherein the one or more anti-human hemoglobin monoclonal antibodies are one of 5C-2A (NPMD accession number NITE BP-02268) or 12-9G-C(NPMD accession number NITE BP-02269).

(16) The immunological measurement method according to (14), wherein the one or more anti-human hemoglobin monoclonal antibodies are two or more selected from the group consisting of 5C-2A (NPMD accession number NITE BP-02268), 7C-7B-8E (NPMD accession number NITE BP-02270), 1-5G-3C (NPMD accession number NITE BP-02271), 12-9G-C(NPMD accession number NITE BP-02269), 79-8G-3F (NPMD accession number NITE BP-02272), and SU112.

(17) The immunological measurement method according to any of (14) to (16), wherein the anti-human hemoglobin monoclonal antibody is derived from a mouse.

(18) The immunological measurement method according to any of (14) to (17), wherein the insoluble carrier particle to which the anti-human hemoglobin monoclonal antibody is immobilized is a latex particle or a metal colloidal particle.

Advantageous Effects of Invention

The present invention enables the specific measurement of a hemoglobin-haptoglobin complex in a test specimen without being affected by free hemoglobin and/or free haptoglobin which are not formed in a complex by using an immunological measurement reagent produced by immobilizing the above anti-human hemoglobin monoclonal antibody to an insoluble carrier particle.

Additionally, the screening examination on digestive organ diseases involving bleeding can thus be carried out easily in a short time for, as a test substance, the hemoglobin-haptoglobin complex, which has superior stability in a sample to hemoglobin.

DESCRIPTION OF EMBODIMENTS

The anti-human hemoglobin monoclonal antibody of an embodiment of the present invention is an anti-human hemoglobin monoclonal antibody wherein a monoclonal antibody-immobilized insoluble carrier particle obtained by immobilizing the monoclonal antibody to an insoluble carrier particle causes an agglutination reaction with a hemoglobin-haptoglobin complex but does not cause an agglutination reaction with hemoglobin.

The anti-human hemoglobin monoclonal antibody of another embodiment of the present invention is an antibody kit, and specifically the antibody kit comprising two or more anti-human hemoglobin monoclonal antibodies wherein one or more monoclonal antibody-immobilized insoluble carrier particles obtained by immobilizing the two or more anti-human hemoglobin monoclonal antibodies to one or more insoluble carrier particles cause an agglutination reaction with a hemoglobin-haptoglobin complex, but do not cause an agglutination reaction with hemoglobin.

The hemoglobin-haptoglobin complex in the present invention is a complex formed by hemoglobin and haptoglobin and more stable than free hemoglobin. When a red blood cell is destroyed for some reason in a blood vessel to release hemoglobin into blood, the released hemoglobin is oxidized and thereby causes oxidative vascular disorder toxicity. It is known that haptoglobin readily then forms a complex with the released hemoglobin and neutralizes the toxicity thereof. Subsequently, the hemoglobin-haptoglobin complex is readily taken in via a receptor of reticuloendothelial cell and subjected to the decomposition process, but it is known that the hemoglobin-haptoglobin complex itself is more stable than hemoglobin.

The specific detection and measurement of the hemoglobin-haptoglobin complex contained in feces in view of the nature that a hemoglobin-haptoglobin complex is a stable structure enable the awareness of bleeding in the digestive tracts.

As the method for detecting and measuring a hemoglobin-haptoglobin complex, an immunological measurement method is preferable, and an immune agglutination reaction method is further preferable as the method of screening examination for a large number of samples in a short time. As the immune agglutination reaction method, a method wherein a carrier particle, for example, a particle carrier of homogeneous system capable of highly sensitive measurement, is used is preferable.

Further, in view of specifically detecting and measuring a hemoglobin-haptoglobin complex, a monoclonal antibody is suitable as the antibody used for the immunological measurement method. The present invention constructs a method for specifically detecting and measuring a hemoglobin-haptoglobin complex by immobilizing, to an insoluble carrier particle, a monoclonal antibody capable of detecting and measuring a hemoglobin-haptoglobin complex when used in the immune agglutination reaction method.

The anti-human hemoglobin monoclonal antibody for constructing the method for specifically detecting and measuring a hemoglobin-haptoglobin complex is not particularly limited by the origin thereof, but an anti-human hemoglobin mouse monoclonal antibody derived from a mouse is preferable.

The anti-human hemoglobin mouse monoclonal antibody can be produced by a conventional production method of a monoclonal antibody. Examples include the following method wherein a mouse is used. Specifically, a mouse is immunized with human hemoglobin, then the enlarged spleen is removed to prepare spleen-derived B cell, the B cell is cell-fused by an electrical fusion method with a separately grown mouse myeloma cell, and the cell made by fusing the B cell and the myeloma cell is grown and cloned using selective medium. Whether the consequently grown colony is producing the antibody to the human hemoglobin is confirmed. The cells for which the production of the antibody to the human hemoglobin has been confirmed are cloned to obtain an anti-human hemoglobin mouse monoclonal antibody producing cell line. The obtained anti-human hemoglobin mouse monoclonal antibody producing cell line is cultured, the culture supernatant or cultured cell thereof is grown within the peritoneal cavity of a mouse to obtain an ascites fluid, and the antibody is purified from the ascites fluid to obtain the anti-human hemoglobin mouse monoclonal antibody.

Subsequently, for the application of the anti-human hemoglobin mouse monoclonal antibody to the immune agglutination reaction method, the antibody is immobilized to an insoluble carrier particle. Examples of the insoluble carrier particle for immobilizing the monoclonal antibody include commonly used latex particles, silica particles, metal colloidal particles, magnetic particles, fluorescent particles, and red blood cells, but are not limited thereto.

Further, the particle size of the insoluble carrier particle is preferably 50 to 500 nm, and further preferably 75 to 350 nm, but are not limited to these ranges, and particle of any particle size can be used.

Furthermore, as for the method of immobilizing the antibody to the insoluble carrier particle, the antibody and the insoluble carrier particle are mixed to cause the physisorption of the antibody onto the surface of the insoluble carrier particle thereby to immobilize the antibody to the insoluble carrier particle, which is a known technique.

Further, when the insoluble carrier particle to the surface of which an amino group or a carboxyl group is introduced is used, the immobilization of the antibody to the surface of the insoluble carrier particle is enabled by a chemical bond using glutaraldehyde or a carboximide reagent.

The insoluble carrier particle to which one or more anti-human hemoglobin monoclonal antibodies are immobilized obtained by these methods is added to a mixture containing free hemoglobin and free haptoglobin which are not formed in a complex and a hemoglobin-haptoglobin complex to confirm that no agglutination reaction is caused with free hemoglobin or free haptoglobin but an agglutination reaction is caused with a hemoglobin-haptoglobin complex, to thereby obtain the anti-human hemoglobin monoclonal antibody and the anti-human hemoglobin monoclonal antibody-immobilized insoluble carrier particle of the present invention.

In other words, the anti-human hemoglobin monoclonal antibody can be obtained which causes the agglutination reaction specifically with a hemoglobin-haptoglobin complex when the antibody is immobilized to the insoluble carrier particle and used, and the anti-human hemoglobin monoclonal antibody-immobilized insoluble carrier particle can be obtained by immobilizing the antibody to an insoluble carrier particle. With these, the measurement reagent specifically reacting to a hemoglobin-haptoglobin complex and containing the antibody or the monoclonal antibody-immobilized insoluble carrier particle, and the measurement method for specifically detecting and measuring a hemoglobin-haptoglobin complex using the antibody or the monoclonal antibody-immobilized insoluble carrier particle can also be obtained.

The anti-human hemoglobin monoclonal antibody of an embodiment of the present invention is preferably 5C-2A deposited under accession number NITE BP-02268 at NPMD or 12-9G-C deposited under accession number NITE BP-02269 at NPMD, which causes the agglutination reaction specifically with a hemoglobin-haptoglobin complex when immobilized to the insoluble carrier particle and used.

Further, the anti-human hemoglobin monoclonal antibody kit of another embodiment of the present invention is preferably two or more selected from the group consisting of 5C-2A deposited under accession number NITE BP-02268 at NPMD, 7C-7B-8E deposited under accession number NITE BP-02270 at NPMD, 1-5G-3C deposited under accession number NITE BP-02271 at NPMD, 12-9G-C deposited under accession number NITE BP-02269 at NPMD, 79-8G-3F deposited under accession number NITE BP-02272 at NPMD, and SU112 (NIPPON BIO-TEST LABORATORIES INC.), which cause the agglutination reaction specifically with a hemoglobin-haptoglobin complex when the two or more monoclonal antibodies are immobilized to the insoluble carrier particle and used.

The measurement reagent of the present invention comprises the anti-human hemoglobin monoclonal antibody or the antibody kit, or the anti-human hemoglobin monoclonal antibody-immobilized insoluble carrier particle, and may also comprise other components such as various electrolytes, a buffer, a stabilizing agent, a surfactant, or a sensitizer.

The measurement method of the present invention is an immunological measurement method for specifically detecting a hemoglobin-haptoglobin complex using a monoclonal antibody-immobilized insoluble carrier particle obtained by immobilizing one or more anti-human hemoglobin monoclonal antibodies to an insoluble carrier particle, and the monoclonal antibody-immobilized insoluble carrier particle causes the agglutination reaction with a hemoglobin-haptoglobin complex but does not cause the agglutination reaction with hemoglobin, whereby only the hemoglobin-haptoglobin complex can specifically be detected and measured from a mixture containing free hemoglobin and free haptoglobin which are not formed in a complex and the hemoglobin-haptoglobin complex.

The measurement method of the present invention specifically detects and measures the hemoglobin-haptoglobin complex in a sample based on the presence or absence of an agglutination reaction when the monoclonal antibody-immobilized insoluble carrier particle and a sample (test specimen) are mixed. The sample is not particularly limited as long as it can contain a hemoglobin-haptoglobin complex, but preferably blood, feces, urine, or sweat, and particularly preferably feces. The detection and measurement method of the agglutination reaction may be a common method, and examples include measurement of absorbance, measurement of scattered light intensity, and visual measurement (slide agglutination method).

Hereinafter, the present invention is specifically described in reference to Examples, but the present invention is not limited to these Examples.

EXAMPLES

Example 1—Production of Anti-Human Hemoglobin Monoclonal Antibody (1) Immunization of Mouse Five each of 7-week old female Balb/c and ddY mice were immunized with hemoglobin. For the immunization protocol, the initial immunization was carried out with a hemoglobin solution mixed with adjuvant in a dose of 50 µg/mouse under the dorsal skin.

Four weeks after the initial immunization, the immunization was carried out with a hemoglobin solution mixed with adjuvant in a dose of 50 µg/mouse under the dorsal skin, and 4 weeks thereafter the immunization was further carried out with a hemoglobin solution mixed with adjuvant in a dose of 50 µg/mouse under the dorsal skin.

After each immunization, an antiserum titer was measured by RIA method of a 2-antibody method using $^{125}$I-labeled hemoglobin. As a result, a high antiserum titer was obtained in one of the ddY mice, which was subjected to cell fusion. Note that no fluctuations in the antiserum titers were confirmed after the second immunization and the third immunization.

(2) Cell Fusion

Three days before the cell fusion was carried out, the final immunization was carried out intraperitoneally with a hemoglobin solution in a dose of 50 µg/mouse. For the cell fusion, the spleen was removed from the mouse with which 16 weeks have passed since the initial immunization, and spleen cell was prepared.

The prepared spleen cell and mouse myeloma NS-1 cell were cell-fused by an electrical fusion method, suspended in selective medium for fused cell, and inoculated in a 96-well microplate.

(3) Screening of Monoclonal Antibody Producing Cell Line

Ten days after the cell fusion, an anti-human hemoglobin monoclonal antibody producing cell was screened by RIA method of a 2-antibody method using $^{125}$I-labeled hemoglobin and a hemoglobin-haptoglobin complex.

Example 2—Binding Specificity of Monoclonal Antibody (1) Selection of Monoclonal Antibodies The total of 46 clones of 45 clones of the anti-human hemoglobin monoclonal antibody obtained by the cell fusion and a commercial anti-human hemoglobin monoclonal antibody SU112 (NIPPON BIO-TEST LABORATORIES INC.) were selected to evaluate the binding specificity to hemoglobin and a hemoglobin-haptoglobin complex.

For the evaluation method, each of the anti-human hemoglobin monoclonal antibodies was immobilized to a polystyrene latex particle, and the degrees of agglutination were compared when the antibody-immobilized latex particle was reacted to the specimen containing hemoglobin and a hemoglobin-haptoglobin complex.

(2) Immobilization of Monoclonal Antibodies to Polystyrene Latex Particle

Each of the monoclonal antibodies was immobilized to a polystyrene latex particle having a particle size of 211 nm.

The immobilization of the antibody to the polystyrene latex particle described above was carried out utilizing a known technique. More specifically, polystyrene latex particles and the antibody were mixed to cause the physisorption of the antibody on the hydrophobic surface of the polystyrene latex particle, whereby the immobilization of the antibody to the polystyrene latex particle was achieved.

(3) Preparation of Specimen

A specimen of the hemoglobin-haptoglobin complex was produced by mixing 32.3 pmol/mL of hemoglobin and haptoglobin in an equimolar thereto in an equal amount of liquid. For the specimen of hemoglobin alone, a specimen containing 16.1 pmol/mL of hemoglobin was used.

(4) Measurement Method of Latex Agglutination

Using wells of a 96-well flat-bottom microplate, the agglutination reaction was carried out. For the specific method, 100 µL of a 50 mM HEPES buffer solution (pH 7.4) was dispensed into each well of the microplate, 50 µL of the polystyrene latex particle solution in which each of the antibodies was immobilized was added, and then 30 µL of the specimen was added.

Using Sunrise Rainbow (Tecan Japan Co., Ltd.), 10 seconds after and 5 minutes 10 seconds after the addition of the specimen, absorbances were measured at a wavelength of 660 nm and the differences thereof were used as the index of the agglutination.

The antibodies or the combinations thereof demonstrating higher degrees of the agglutination when reacted to the hemoglobin-haptoglobin complex compared with the degrees of the agglutination when reacted to hemoglobin are shown in Table 1. These antibodies were deposited at NITE Patent Microorganisms Depositary (NPMD). When the monoclonal antibodies or the combinations thereof shown in Table 1 are used, the reagent capable of specifically measuring the hemoglobin-haptoglobin complex is expected. It was confirmed that the monoclonal antibodies of 5C-2A (NPMD accession number NITE BP-02268) and 12-9G-C (NPMD accession number NITE BP-02269) are hardly affected by hemoglobin even when used singly and agglutinate with the hemoglobin-haptoglobin complex. Further, it was confirmed that the combination of 1-5G-3C (NPMD accession number NITE BP-02271) and SU112 (NIPPON BIO-TEST LABORATORIES INC.), the combination of 5C-2A (NPMD accession number NITE BP-02268) and 79-8G-3F (NPMD accession number NITE BP-02272), the combination of 5C-2A (NPMD accession number NITE BP-02268) and 7C-7B-8E (NPMD accession number NITE BP-02270), the combination of 5C-2A (NPMD accession number NITE BP-02268) and 79-8G-3F, and the combination of 12-9G-C (NPMD accession number NITE BP-02269) and 79-8G-3F (NPMD accession number NITE BP-02272) are hardly affected by hemoglobin and agglutinate with the hemoglobin-haptoglobin complex.

TABLE 1

| Combination of monoclonal antibodies | | Hemoglobin (ΔAbs. × 10000) | Hemoglobin-haptoglobin complex (ΔAbs. × 10000) |
|---|---|---|---|
| 1-5G-3C | SU112 | 0 | 710 |
| 5C-2A | Single | 290 | 1100 |
| 5C-2A | 79-8G-3F | 0 | 670 |
| 5C-2A | 7C-7B-8E | 390 | 940 |
| 7C-7B-8E | 79-8G-3F | 0 | 520 |
| 12-9G-C | Single | 280 | 1040 |
| 12-9G-C | 79-8G-3F | 0 | 550 |

Example 3—Specific Reaction to Hemoglobin-Haptoglobin Complex (1)

(1) Preparation of Monoclonal Antibody-Immobilized Latex Solution

The monoclonal antibody of 5C-2A was immobilized to the latex particles by the same method as in Example 2 to prepare a latex solution.

(2) Preparation of Hemoglobin-Haptoglobin Complex Specimen

Solutions containing 11.4 pmol/mL of hemoglobin and 0.0, 3.8, 7.5, or 11.3 pmol/mL of haptoglobin in a 50 mM phosphate buffer solution (pH 6.6) were prepared. More specifically, due to the strong binding property of hemoglobin and haptoglobin, the solutions theoretically containing 0.0 and 11.4 pmol/mL, 3.8 and 7.6 pmol/mL, 7.5 and 3.9 pmol/mL, and 11.3 and 0.1 pmol/mL of the hemoglobin-haptoglobin complex and hemoglobin, respectively, were prepared.

(3) Reaction of Monoclonal Antibody-Immobilized Latex Particle to Hemoglobin-Haptoglobin Complex The reaction of monoclonal antibody-immobilized latex particle to the hemoglobin-haptoglobin complex was confirmed using a 7170S type Automatic Analyzer (manufactured by Hitachi High-Technologies Corporation). For the measurement method, 15 μL of the hemoglobin-haptoglobin complex-containing solution was added to a reaction cell of H7170S, then 100 μL of a 50 mM HEPES buffer solution (pH 7.4) was added thereto, and subsequently 25 μL of the monoclonal antibody-immobilized latex solution was added thereto, whereby amounts of turbidity variation at a wavelength of 660 nm for a period of 440 seconds were determined.

Table 2 shows turbidity variation rates of the solutions when the amount of turbidity variation at which haptoglobin was added so as to be 0 pmol/mL was corrected to 0 and the amount of turbidity variation at which haptoglobin was added so as to be 11.3 pmol/mL was taken as 100%.

With increase of the concentration of haptoglobin added, more specifically, the concentration of hemoglobin-haptoglobin complex, the turbidity variation due to the latex agglutination caused by the antigen-antibody reaction with the monoclonal antibody immobilized to the latex particle increases. Further, the turbidity variation due to the latex agglutination was low at a low concentration of haptoglobin added, and thus it was inferred that the reaction to the hemoglobin which did not bind to haptoglobin was not confirmed. Based on these, when the monoclonal antibody of 5C-2A was used, the specific detection of the hemoglobin-haptoglobin complex is enabled.

TABLE 2

| Hemoglobin (pmol/mL) | Haptoglobin (pmol/mL) | Amount of turbidity variation (%) |
|---|---|---|
| 11.4 | 0.0 | 0.0 |
| 11.4 | 3.8 | 10.2 |
| 11.4 | 7.5 | 53.7 |
| 11.4 | 11.3 | 100.0 |

Example 4—Specific Reaction to Hemoglobin-Haptoglobin Complex (2)

(1) Preparation of Monoclonal Antibody-Immobilized Latex Solution

The monoclonal antibodies of 1-5G-3C, 7C-7B-8E, SU112, and 79-8G-3F were immobilized to the latex particle by the same method as in Example 2 to prepare latex solutions. Subsequently, latex solutions containing combinations of 1-5G-3C and SU112 and 7C-7B-8E and 79-8G-3F were produced and subjected to the test.

(2) Preparation of Hemoglobin-Haptoglobin Complex Specimen

Specimens were prepared by the same method as in Example 3 except that solutions contained 13.0 pmol/mL of hemoglobin and 0.0, 9.4, 11.3, or 13.0 pmol/mL of haptoglobin. More specifically, the solutions theoretically containing 0.0 and 13.0 pmol/mL, 9.4 and 3.6 pmol/mL, 11.3 and 1.7 pmol/mL, and 13.0 and 0.0 pmol/mL of the hemoglobin-haptoglobin complex and hemoglobin, respectively, were prepared.

(3) Reaction of Monoclonal Antibody-Immobilized Latex Particle to Hemoglobin-Haptoglobin Complex The amounts of turbidity variation were determined by the same method as in Example 3.

Table 3 shows turbidity variation rates of the solutions when the amount of turbidity variation at which haptoglobin was added so as to be 0 pmol/mL was corrected to 0 and the amount of turbidity variation of a solution prepared so as to contain hemoglobin and haptoglobin in equal amounts at which haptoglobin was added so as to be 13.0 pmol/mL was taken as 100%.

The same results as in Example 3 were obtained. More specifically, with increase of the concentration of haptoglobin added, more specifically, the concentration of hemoglobin-haptoglobin complex, the turbidity variation due to the latex agglutination caused by the antigen-antibody reaction with the monoclonal antibody immobilized to the latex particle increased. Based on these, when the combination of 1-5G-3C and SU112 and the combination of 7C-7B-8E and 79-8G-3F are used, the specific detection of the hemoglobin-haptoglobin complex is enabled.

TABLE 3

| Hemoglobin (pmol/mL) | Haptoglobin (pmol/mL) | Amount of turbidity variation (%) | |
|---|---|---|---|
| | | 1-5G-3C + SU112 | 7-7B-8E + 79-8G-3F |
| 13.0 | 0.0 | 0 | 0 |
| 13.0 | 9.4 | 49 | 69 |
| 13.0 | 11.3 | 68 | 73 |
| 13.0 | 13.1 | 100 | 100 |

Comparative Example 1 Measurement of Hemoglobin and Hemoglobin-Haptoglobin Complex by ELISA Method The combination of 5C-2A and 79-8G-3F, wherein the agglutination reaction was not caused when reacted to hemoglobin but the specific reaction to the hemoglobin-haptoglobin complex was confirmed in Example 2, was evaluated by ELISA method on the binding specificity to hemoglobin and the hemoglobin-haptoglobin complex.
(1) Preparation of Monoclonal Antibody-Immobilized Latex Solution 5C-2A was solid-phased on a 96-well microplate to prepare a solid-phased plate, and 79-8G-3F was labeled with horseradish peroxidase to prepare an enzyme-labeled substance. The antibody was solid-phased on the 96-well microplate utilizing a known technique. More specifically, the antibody was added to the 96-well microplate to cause the physisorption of the antibody onto the hydrophobic surface of the 96-well microplate, whereby the antibody was solid-phased on the 96-well microplate.
(2) Preparation of Hemoglobin-Haptoglobin Complex Specimen A solution containing 12.6 pmol/mL of hemoglobin and 12.6 pmol/mL of haptoglobin in a 50 mM phosphate buffer solution (pH 6.6) was prepared, and the solution was doubling-diluted with a 50 mM phosphate buffer solution (pH 6.6) to prepare specimens containing 1.6, 3.2, 6.3, or 12.6 pmol/mL of hemoglobin-haptoglobin complex.
(3) Measurement Method by ELISA 10 µL of the standard solution or the sample was added to a 96-well microplate, stirred for 3 minutes, and then left to stand at 25° C. for 60 minutes. After left to stand, the microplate was washed 3 times using a surfactant-containing 50 mM phosphate buffer solution (pH 7.4).

After washing, 100 µL of the enzyme-labeled substance was added to the 96-well microplate, stirred for 3 minutes, and then left to stand at 25° C. for 60 minutes. After left to stand, the microplate was washed 3 times using a surfactant-containing 50 mM phosphate buffer solution (pH 7.4).

After washing, 100 µL of a 0.4 mg/mL o-phenylenediamine-containing substrate solution was added to the 96-well microplate and left to stand at 25° C. for 14 minutes. After left to stand, 100 µL of 3N sulfuric acid was added as a reaction stop solution.

The measurement was carried out using Sunrise Rainbow (Tecan Japan Co., Ltd.) at a measurement wavelength of 492/650 nm. Table 4 shows the measurement results by ELISA method using the combination of 5C-2A and 79-8G-3F, wherein the agglutination reaction was not caused when reacted to hemoglobin but the specific reaction to the hemoglobin-haptoglobin complex was confirmed when the antibodies were immobilized to the insoluble carrier such as latex and used. In ELISA method wherein the combination of 5C-2A and 79-8G-3F was used, the antibodies reacted to both hemoglobin and the hemoglobin-haptoglobin complex and failed to specifically detect the hemoglobin-haptoglobin complex.

TABLE 4

| Concentration* (pmol/mL) | Hemoglobin ($\Delta$Abs. × 10000) | Hemoglobin-haptoglobin complex ($\Delta$Abs. × 10000) |
|---|---|---|
| 1.6 | 6672 | 11165 |
| 3.2 | 9632 | 16668 |
| 6.3 | 12282 | 21758 |
| 12.6 | 14382 | 24458 |

*Concentration of hemoglobin or hemoglobin-haptoglobin complex

Example 5—Specific Reaction to Hemoglobin-Haptoglobin Complex (3)

The combination of 5C-2A and 79-8G-3F, wherein the agglutination reaction was not caused when reacted to hemoglobin but the specific reaction to the hemoglobin-haptoglobin complex was confirmed in Example 2, was evaluated by the latex agglutination method on the binding specificity to hemoglobin and the hemoglobin-haptoglobin complex.
(1) Preparation of Monoclonal Antibody-Immobilized Latex Solution The monoclonal antibodies of 5C-2A and 79-8G-3F were immobilized to the latex particles by the same method as in Example 2 to prepare latex solutions. The latex solutions in which the monoclonal antibodies of 5C-2A and 79-8G-3F were immobilized were mixed and subjected to the test.
(2) Preparation of Hemoglobin-Haptoglobin Complex Specimen A solution containing 12.6 pmol/mL of hemoglobin and 12.6 pmol/mL of haptoglobin in a 50 mM phosphate buffer solution (pH 6.6) was prepared, and the solution was doubling-diluted with a 50 mM phosphate buffer solution (pH 6.6) to prepare specimens containing 1.6, 3.2, 6.3, or 12.6 pmol/mL of the hemoglobin-haptoglobin complex.
(3) Measurement Method of Latex Agglutination Method A 50 mM HEPES buffer solution (pH 7.4) was used as R1 and the above monoclonal antibody-immobilized latex solution was used as R2. The measurement was carried out using a Hitachi 7170S type Automatic Analyzer (manufactured by Hitachi High-Technologies Corporation). For the measurement method, 15 µL of the standard solution or the sample was added to a reaction cell, then 100 µL of a 50 mM HEPES buffer solution (pH 7.4) was added thereto, and subsequently 25 µL of the monoclonal antibody-immobilized latex solution was added thereto, whereby amounts of turbidity variation at a wavelength of 660 nm for a period of 440 seconds were measured.
(4) Reaction of Monoclonal Antibody-Immobilized Latex Particle to Hemoglobin-Haptoglobin Complex Table 5 shows the measurement results by the latex agglutination method using the combination of 5C-2A and 79-8G-3F, which was confirmed to have reacted to both hemoglobin and the hemoglobin-haptoglobin complex in ELISA method. The combination of 5C-2A and 79-8G-3F was confirmed that the agglutination reaction was not caused when reacted to hemoglobin but the specific reaction to the hemoglobin-haptoglobin complex was confirmed when the antibodies were immobilized to the insoluble carrier such as latex.

TABLE 5

| Concentration* (pmol/mL) | Hemoglobin (ΔAbs. × 10000) | Hemoglobin-haptoglobin complex (ΔAbs. × 10000) |
|---|---|---|
| 1.6 | −15 | −2 |
| 3.2 | −15 | 53 |
| 6.3 | −1 | 199 |
| 12.6 | 11 | 652 |

*Concentration of hemoglobin or hemoglobin-haptoglobin complex

Example 6—Measurement of Sample (1)

Using ELISA method, one of the conventional methods, and the method of the present invention, the measurement of the hemoglobin-haptoglobin complex was carried out.
(1) Measurement of Hemoglobin-Haptoglobin Complex by ELISA Method The anti-human haptoglobin monoclonal antibody was solid-phased on a 96-well microplate to prepare a solid-phased plate, and the anti-human hemoglobin polyclonal antibody was labeled with horseradish peroxidase to prepare an enzyme-labeled substance.

100 μL of a 50 mM phosphate buffer solution (pH 7.2) and 10 μL of the standard solution or the sample were added to a 96-well microplate, stirred for 5 minutes, and then left to stand at 25° C. for 120 minutes. After left to stand, the microplate was washed 3 times using a surfactant-containing 50 mM phosphate buffer solution (pH 7.5).

After washing, 100 μL of the enzyme-labeled substance was added to the 96-well microplate, stirred for 5 minutes, and then left to stand at 25° C. for 55 minutes. After left to stand, the microplate was washed 3 times using a surfactant-containing 50 mM phosphate buffer solution (pH 7.5).

After washing, 100 μL of a 0.4 mg/mL o-phenylenediamine-containing substrate solution was added to the 96-well microplate and left to stand at 25° C. for 15 minutes. After left to stand, 100 μL of 2N sulfuric acid was added as a reaction stop solution.

The measurement was carried out at a measurement wavelength of 492/650 nm using Sunrise Rainbow (Tecan Japan Co., Ltd.), and the measurement value of the sample was determined based on the calibration curve obtained from the measurement result of the standard solution.
(2) Measurement of Hemoglobin-Haptoglobin Complex by Latex Agglutination Method A 50 mM HEPES buffer solution (pH 7.4) was used as R1 and the monoclonal antibody-immobilized latex solution of Example 3 was used as R2.

Figure 1:
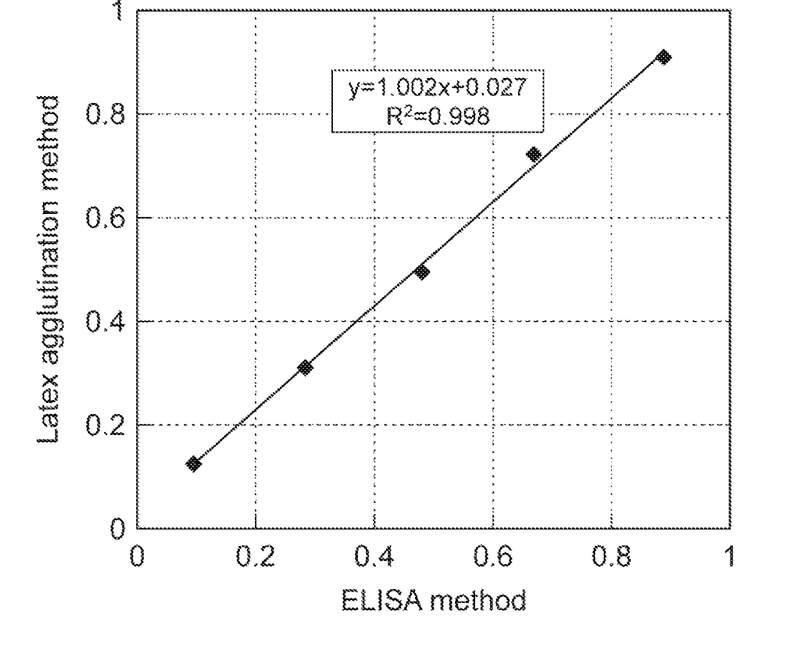
FIG. 1—A correlation chart of samples when measured by ELISA method and the latex agglutination method.

The measurement was carried out using JCA-BM2250 (JEOL Ltd.). For the measurement method, 8 μL of the standard solution or the sample was added to a reaction cell, then 50 μL of R1 was added thereto, and subsequently 16.7 μL of R2 was added thereto, whereby an amount of turbidity variation at a wavelength of 658 nm for a period of 471 seconds was measured, and the measurement value of the sample was determined based on the calibration curve obtained from the measurement result of the standard solution.
(3) Measurement Results The measurement results on 5 samples by ELISA and the latex agglutination method are shown in Table 6, and the correlation diagram between the measurements is shown in FIG. 1.

The measurement results on the samples by the latex agglutination method were equal to the measurement results of the samples by ELISA, and the correlation coefficient was 0.998, which was satisfactory. Note that the numerical value 1 in FIG. 1 indicates the concentration of 12.9 pmol/mL in terms of hemoglobin.

TABLE 6

| Sample | ELISA method | Latex agglutination method |
|---|---|---|
| A | 0.09 | 0.12 |
| B | 0.28 | 0.31 |
| C | 0.48 | 0.49 |
| D | 0.67 | 0.72 |
| E | 0.89 | 0.91 |

These results revealed that the accurate measurement of the hemoglobin-haptoglobin complex in a sample is enabled by using the present invention and contributes to the diagnosis of diseases.

INDUSTRIAL APPLICABILITY

The present invention provides a monoclonal antibody or an antibody kit capable of specifically detecting and measuring a hemoglobin-haptoglobin complex when immobilized to an insoluble carrier particle and used, and an insoluble carrier particle to which the monoclonal antibody is immobilized, and a measurement reagent and a measurement method for specifically detecting and measuring a hemoglobin-haptoglobin complex in a sample using the same. The application of this invention to a feces sample enables the examination on the presence or absence of bleeding in the digestive organs in a short time accurately.

Antibody Deposits

The novel antibodies of the invention were deposited to NITE (National Institute of Technology and Evaluation, 2-49-10, Nishihara, Shibuya-ku, Tokyo 151-0066 Japan) Patent Microorganisms Depository on May 27, 2016, which deposits were assigned an international accession number under the Budapest Treaty on Apr. 3, 2017. The receipt numbers indicating proof of deposit on May 27, 2016, and the Accession numbers assigned on Apr. 3, 2016 are indicated in Table 7 below.

TABLE 7

| Antibody Name | Receipt Number | Accession Number |
|---|---|---|
| 5C-2A | NITE ABP-02268 | NITE BP-02268 |
| 7C-7B-8E | NITE ABP-02270 | NITE BP-02270 |
| 1-5G-3C | NITE ABP-02271 | NITE BP-02271 |
| 12-9G-C | NITE ABP-02269 | NITE BP-02269 |
| 79-8G-3F | NITE ABP-02272 | NITE BP-02272 |

The invention claimed is:
1. An antibody kit comprising monoclonal antibody-immobilized insoluble carrier particles, wherein one or more antibodies selected from the group consisting of 5C-2A deposited under NPMD accession number NITE BP-02268, 7C-7B-8E deposited under NPMD accession number NITE BP-02270, 1-5G-3C deposited under NPMD accession number NITE BP-02271, 12-9G-C deposited under NPMD accession number NITE BP-02269 and 79-8G-3F deposited under NPDM accession number NITE BP-02272, are immobilized on the insoluble carrier particles.

2. The kit of claim 1, wherein the monoclonal antibody-immobilized insoluble carrier particles are latex particles or metal colloidal particles.

3. An anti-human hemoglobin monoclonal antibody, wherein the antibody is selected from the group consisting of 5C-2A deposited under NPMD accession number BP-02268, 7C-7B-8E deposited under NPMD accession number NITE-02270, 1-5G-3C deposited under NPMD accession number NITE BP-02271, 12-9G-C deposited under NPMD accession number NITE BP-02269, or 79-8G-3F deposited under NPMD accession number NITE BP-02272.

4. An immunological agglutination measurement method for specifically detecting a hemoglobin-haptoglobin complex, the method comprising:

mixing a sample with monoclonal antibody-immobilized insoluble carrier particles, wherein the monoclonal antibody-immobilized insoluble carrier particles comprise one or more immobilized anti-human hemoglobin monoclonal antibodies, wherein the one or more anti-human hemoglobin monoclonal antibodies are selected from the group consisting of 5C-2A deposited under NPMD accession number NITE BP-02268 or 12-9G-C deposited under NPMD accession number NITE BP-02269, or wherein the monoclonal-antibody immobilized carrier particles comprise two or more immobilized anti-human hemoglobin monoclonal antibodies, wherein the two or more anti-human hemoglobin monoclonal antibodies are selected from the group consisting of 5C-2A deposited under NPMD accession number NITE BP-02268, 7C-7B-8E deposited under NPMD accession number NITE BP-02270, 1-5G-3C deposited under NPMD accession number NITE BP-02271, 12-9G-C deposited under NPMD accession number NITE BP-02269, and 79-8G-3F deposited under NPMD accession number NITE BP-02272, and detecting agglutination reaction.

5. The immunological agglutination measurement method of claim 4, wherein the insoluble carrier particles are latex particles or metal colloidal particles.

* * * * *